United States Patent [19]

Francis

[11] Patent Number: 4,990,271

[45] Date of Patent: Feb. 5, 1991

[54] ANTIWEAR, ANTIOXIDANT AND FRICTION REDUCING ADDITIVE FOR LUBRICATING OILS

[75] Inventor: James N. Francis, Maplewood, N.J.

[73] Assignee: Exxon Research and Engineering Company, Florham Park, N.J.

[21] Appl. No.: 404,142

[22] Filed: Sep. 7, 1989

[51] Int. Cl.$^5$ ............................................ C10M 135/14
[52] U.S. Cl. .................... 252/33.6; 252/42.7; 252/46.4; 252/49.7
[58] Field of Search ................ 252/49.7, 46.4, 46.3

[56] References Cited

U.S. PATENT DOCUMENTS 2,951,040  8/1960  Hugel ............................... 252/33.6
3,419,589  12/1968  Larson ............................. 252/33.6
3,840,463  10/1974  Froeschmann ..................... 252/42.7

Primary Examiner—Jacqueline V. Howard
Attorney, Agent, or Firm—Joseph J. Dvorak

[57] ABSTRACT

A lubricating oil composition is provided which comprises a major amount of an oil of lubricating viscosity and a minor amount of an additive formed by contacting molybdenum hexacarboxyl with dixanthogens of the formula $(ROCS_2)_2$ wherein the R is an organo group having a sufficient number of carbon atoms to render the additive formed soluble in the oil. In general, R is the same or different alkyl, aralkyl, and alkoxylalkyl groups having from about 2 to about 20 carbon atoms and preferably R is an alkyl group having from about 4 to about 12 carbon atoms.

20 Claims, No Drawings

ANTIWEAR, ANTIOXIDANT AND FRICTION REDUCING ADDITIVE FOR LUBRICATING OILS

FIELD OF THE INVENTION

The present invention is concerned with improved lubricating compositions. Indeed, the present invention relates to novel molybdenum and sulfur containing additives for lubricants and to lubricant compositions containing the novel additives.

BACKGROUND OF THE INVENTION

Molybdenum disulfide is a known lubricant additive. Unfortunately, it has certain known disadvantages which are associated with the fact that it is insoluble in lubricating oils. Therefore, oil-soluble molybdenum and sulfur containing compounds have been proposed and investigated as lubricant additives. For example, in U.S. Pat. No. 2,951,040 an oil soluble molybdic xanthate is disclosed as being useful in lubricating compositions. Apparently, the molybdic xanthate decomposes under conditions of use to form an oil insoluble solid molybdenum sulfide on the metal surfaces being lubricated.

U.S. Pat. No. 3,419,589 discloses the use of certain sulfurized molybdenum (IV) dialkyl dithiocarbamates as lubricant additives. These additives are described as being oil soluble or at least capable of being easily suspended in oils.

U.S. Pat. No. 3,840,463 discloses the use of certain metal dialkyl dithiocarbamates or dithiophosphates in combination with metal-free additives containing sulfur and phosphorous.

The foregoing patents are listed as representative of the very many known molybdenum and sulfur containing lubricant additives.

As is known in the art, some lubricant additives function as antiwear agents, some as anti-friction agents, and some as extreme pressure agents. Indeed, some additives may satisfy more than one of these functions. For example, metal dialkyl dithiophosphates represent a class of additives which are known to exhibit antioxidant and antiwear properties. The most commonly used additives in this class are the zinc dialkyldithiophosphates. These compounds provide excellent oxidation resistance and exhibit superior antiwear properties. Unfortunately, they do not have the most desirable lubricity. Therefore, lubricating compositions containing these zinc compounds also require the inclusion of antifriction agents. This leads to other problems in formulating effective lubricant compositions.

Additionally, extreme care must be exercised in combining various additives to assure both compatibility and effectiveness. For example, antifriction agents affect the metal surfaces differently than antiwear agents. If each type of additive is present in a lubricant composition, each may compete for the surface of the metal parts which are subject to lubrication. This can lead to a lubricant that is less effective than expected based on the properties of the individual additive components.

Thus, there remains a need for an improved lubricating compositions based on standard lubricating oils and containing other conventional lubricant additives.

SUMMARY OF THE INVENTION

A lubricating oil composition is provided which comprises a major amount of an oil of lubricating viscosity and a minor amount of an additive formed by reacting molybdenum hexacarbonyl with dixanthogens of the formula $(ROCS_2)_2$ wherein the R is an organo group having a sufficient number of carbon atoms to render the additive formed soluble in the oil. In general, R is the same or different alkyl, aralkyl, and alkoxylalkyl groups having from about 2 to about 20 carbon atoms and preferably R is an alkyl group having from about 4 to about 12 carbon atoms.

The amount of additive is in the range from about 0.01 to about 2.0 weight percent based on the weight of the oil, and preferably, is in the range from about 0.1 to about 1.0 weight percent.

The lubricant compositions according to this invention have excellent antiwear, antioxidant and friction reducing properties. Moreover, the lubricant compositions of the present invention do not include phosphorous. The presence of phosphorous in lubricating oils formulated for automobiles having exhaust gas catalytic reactors is preferably minimized because of the poisoning effect phosphorous has on the catalyst. Finally, the lubricant compositions of the present invention are compatible with other standard additives used in formulating commercial lubricating compositions.

DETAILED DESCRIPTION OF THE INVENTION

The lubricant compositions of the present invention include a major amount of oil of lubricating viscosity. This oil may be selected from naturally occurring mineral oils or from synthetic oils. The oils may range in viscosity from light distillate mineral oils to heavy lubricating oils, such as gas engine oil, mineral lubricating oil, passenger car oils and heavy duty oils. In general, the viscosity of the oil will range from about 5 to about 26 centistokes at 100° C. and especially in the range of 10 to 18 centistokes at 100° C.

The lubricant composition of the present invention includes a minor but effective amount of an additive formed by reacting molybdenum hexacarbonyl, Mo(CO)$_6$, with a dixanthogen, $(ROCS_2)_2$. The reaction is conducted at temperatures ranging from about ambient room temperature to about 140° C., especially between about 80° C. to about 120° C. for times ranging from about 2 to about 10 hours. For example, the Mo(CO)$_6$ and the dixanthogen may be refluxed in toluene for times ranging from about 2 to about 8 hours. The reaction time and temperature will depend upon the dixanthogen selected and the solvent used for carrying out the reaction. Suffice it to say that the reaction is conducted for a time sufficient to form the additive. Useful solvents for carrying out the reaction include aromatic hydrocarbons, especially toluene.

Dixanthogens especially useful in the practice of the present invention can be represented by the formula $(ROCS_2)_2$ in which R can be the same or different organo groups selected from alkyl, aralkyl and alkoxyalkyl group having a sufficient number of carbon atoms to render the additive that is formed soluble in a lubricating oil. Preferably R will have from 2 to 20 carbon atoms. Indeed, it is particularly preferred that R is an alkyl group having from 2 to 20 carbon atoms and especially from 4 to 12 carbon atoms.

In forming the additive of the present invention, the mole ratio of dixanthogen to molybdenum hexacarbonyl should be greater than about 1.5 to 1. For example, in preparing the additive it is preferred to use mole ratios of $(ROCS_2)_2$ to Mo(CO)$_6$ in the range of from about 1.6:1 to about 2:1.

Depending primarily upon the time and temperature at which the $Mo(CO)_6$ and $(ROCS_2)_2$ are reacted, the molybdenum and sulfur containing additive that forms is a brown compound, a purple compound or a mixture of both. Shorter reaction times, e.g., four hours or less, favor the formation of the purple compound. Longer reaction times, e.g., four hours or more, favor formation of the brown compound. For example, when $(C_8H_{17}OCS_2)_2$ is reacted with $Mo(CO)_6$ in toluene for four hours at 100° C. to 110° C., most of the starting material is converted to the purple compound, with virtually none of the brown being present. Continued heating of the reaction mixture results in conversion of the purple compound to the brown compound; indeed, after about six or seven hours, the purple form is largely converted to the brown.

In general, it is preferred to contact the $Mo(CO)_6$ and dixanthogen for a time sufficient for reaction to occur, but generally less than about 7 hours. Beyond 7 hours, undesirable solids begin to form. In order to maximize the formation of additive and minimize formation of undesirably solid by-products, it is preferred to react the $Mo(CO)_6$ and dixanthogen at temperatures of about 100° C. to about 120° C. for times ranging from about five to six hours, thereby producing reaction mixtures which contain both the brown and purple additives of this invention. This is no disadvantage because both forms are effective lubrication additives, and mixtures of the two species (brown and purple) perform as well as either species by itself.

The additives formed with R groups between about $C_4H_9$ and about $C_{14}H_{29}$ can be readily separated from oily organic by-products of the reaction by extracting the oily by-products with moderately polar solvents as acetone, ethyl alcohol, or iso-propyl alcohol. The additives with these R groups are substantially insoluble in such solvents, while the oily by-products are soluble. Separation of the additives from the by-products, however, is not necessary because the by-products do not detract from the beneficial functional properties of the additives.

The physical properties of the purple and brown additives vary with the R group. For example, the additive is crystalline solid when R is $C_2H_5$ and the additive is an amorphous solid when R is larger than about $C_7H_{15}$.

The purple compound formed in reacting $Mo(CO)_6$ with $(ROCS_2)_2$ is a thiocubane of the formula $Mo_4S_4(ROCS_2)_6$.

The brown compound formed in reacting $Mo(CO)_6$ with $(ROCS_2)_2$ is also believed to have a structure very similar to the thiocubane structure of the purple compound based on its ease of formation from the purple compound and chemical analysis.

The above described molybdenum-containing compounds are effective as additives in lubricating compositions when they are used in amounts ranging from about 0.01 to about 2.0 of weight percent, based on the weight of lubricating oil, and preferably at concentrations ranging from about 0.1 to about 1.0 weight percent.

Concentrates of the additive of the present invention in a suitable diluent hydrocarbon diluent provide a convenient means of handling the additives before their use. These concentrates may contain about 1 to about 90 weight percent of the additive based on the weight of diluent, although it is preferred to maintain the additive concentration between about 30 and 60 weight percent. Preferred diluents are selected from hydrocarbons in which the additive is soluble, like toluene, xylene and aromatic oils.

If desired, other known lubricant additives can be used for blending in the lubricant composition of this invention. These include: ashless dispersants, detergents, pour point depressants, viscosity improvers and the like. These can be combined in proportions known in the art.

The invention will be more fully understood by reference to the following examples illustrating various modifications of the invention, which should not be construed as limiting the scope thereof.

EXAMPLE 1

A mixture of 717 grams (1.75 moles) of octyl dixanthogen, $(C_8H_{17}OCS_2)_2$, 263 grams (1 mole) of molybdenum hexacarbonyl, $Mo(CO)_6$, and two liters of toluene was heated to 100° C. with stirring sufficient to agitate the heavy $Mo(CO)_6$ crystals, which did not completely dissolve. The temperature was gradually raised to 110° C. (refluxing the toluene) over a period of five hours, during which time 6 moles (about 150 liters) of carbon monoxide were liberated. The solution turned purple, and all the $Mo(CO)_6$ dissolved. The toluene was removed under a stream of nitrogen while maintaining the temperature of the solution below 80° C. A purple oil solidifying at about room temperature was obtained which was extracted twice with 10 times the volume of isopropyl alcohol containing 10% acetone. The alcohol insoluble solid was separated by filtration, washed with ten times its weight of cold hexane and then dried.

| Elemental Analysis | % Mo | % S | % C | % H |
|---|---|---|---|---|
| Found | 22.49 | 29.42 | 37.26 | 6.09 |
| Calc'd for $Mo_4S_4(C_8H_{17}OCS_2)_6$ | 22.04 | 29.39 | 37.20 | 5.86 |

A chromatogram of the product was obtained as follows. A small spot of the sample was placed on a $2 \times 6$ cm piece of a commercially available silica gel chromatography medium. It was developed with a mixture of 30% toluene and 70% heptane. A dark purple spot at a retention factor (RF) of about 0.6 was observed, and a very faint brown spot remained near the origin.

Following a substantially similar procedure, ethyl dixanthogen, $(C_2H_5OCS_2)_2$ was reacted with $Mo(CO)_6$ to yield a purple compound whose x-ray structural analysis, after separation and purification, showed the compound to be a thiocubane, $Mo_4S_4(C_2H_5OCS_2)_2$.

EXAMPLE 2

The procedure of Example 1 was carried out, except that the reaction mixture was heated for a total of 7 hours. At the end of the heating time, the reaction mixture was allowed to cool to ambient temperature overnight. The mixture was filtered to remove any insoluble material formed, and the toluene removed and the brown residue was extracted as in Example 1. A thin layer chromatogram of the brown solid was obtained. The chromatogram, as in Example 1, showed little or no purple spot at a retention factor of 0.6, but a large dark brown spot near the origin.

Elemental analysis also was obtained with the results shown below.

| Elemental Analysis | % Mo | % S | % C | % H |
| --- | --- | --- | --- | --- |
| Found | 26.23 | 31.91 | 34.38 | 5.61 |

EXAMPLE 3

The procedure of Example 1 was carried out, except that the reaction mixture was heated for a total of 6 hours. The toluene was removed as in Example 1 to yield a brownish-purple oil that partially solidifies upon standing at room temperature for some time. Chromatography as in Example 1 reveals the presence of both a purple spot at RF 0.6, and a brown spot near the origin. Exposure of the developed chromatogram to iodine vapors formed an orange-brown spot at RF 0.75 due to the organic by-products of the reaction mixture.

EXAMPLES 4 AND 5

In these Examples the additive of the invention was evaluated for wear protection using the Four Ball Wear Test procedure (ASTM Test D2266). In Example 4, the sample tested consisted of the Solvent 150 Neutral lubricating oil containing 1 weight percent of the additive prepared in Example 3. In Example 5, a commercially available formulated motor oil without the ZDDP and antioxidants but containing 1 weight percent of the additive prepared in Example 1 was evaluated. The results are given in Table I.

COMPARATIVE EXAMPLES 6 AND 7

In these tests, for comparative purposes, Solvent 150 Neutral oil and a commercially formulated oil were subjected to the Four Ball Wear Test procedure (ASTM Test D2266). The results are shown in Table I.

TABLE I

| Test Run | Oil | Four Ball Wear Volume $MM^3 \times 10^4$ |
| --- | --- | --- |
| (1) Ex. 4 | S150 1% Ex. 3 additive | 28 |
| (2) Ex. 5 | Commercial oil without ZDDP and antioxidants and 1% Ex. 1 additive | 6 |
| (3) Comp. Ex. 6 | S150N | 540 |
| (4) Comp. Ex. 7 | Commercially available oil with ZDDP and antioxidants | 14 |

EXAMPLES 8 TO 12

Following the procedure outlined in Example 1, five additives according to this invention were formed using dixanthogens with the 5 different R groups shown in Table II below. The same 1.75:1 mole ratio of dixanthogen to $Mo(CO)_6$ was used in all 5 runs, which all yielded a purple solid. The additives were all found to be effective in the Four-Ball Wear Test (ASTM D2266). The results are given in Table II.

TABLE II

| Run | Wt % Additive | R in $(ROCS_2)_2$ of Additive | Four Ball Wear Volume $MM^3 \times 10^4$ |
| --- | --- | --- | --- |
| Ex. 8 | .33 | Ethyl | 3 |
| Ex. 9 | .50 | Hexyl | 6 |
| Ex. 10 | .41 | sec-isohexyl | 5 |
| Ex. 11 | .44 | 2-butoxyethyl | 60 |
| Ex. 12 | .56 | Iso-tridecyl | 21 |

EXAMPLE 13

In this example, a lubricating composition of the invention was prepared and tested using the Renault R14 Engine Wear Test.

The oil consisted of a fully formulated commercial motor oil containing 0.59 wt % ZDDP. It also contained 0.5 wt % of the additive of Example 3. The test was carried out by mounting a Renault R14 overhead cam cylinder head via a custom made adaptor plate to a motored rig. The cylinder head angles, oil and coolant supplies are the same as the installed engine.

This test lasts 20 hours during which the oil temperature is maintained at 110° C., the valve spring lead at 1100 Newtons. The camshaft is operated at two speeds, 375 and 750 RPM. The lower speed is maintained for one minute, the higher speed for two minutes, this cycle being repeated for twenty hours. At the conclusion of the test, the weight loss of each of 16 rocker arms is measured. In this test, a rocker arm weight loss exceeding 15 mg is considered to be test failure. In the absence of total failure, the weight loss is averaged.

The results are shown in Table III.

TABLE II

| Run | Rocker Arm Weight Loss Average | Maximum |
| --- | --- | --- |
| Ex. 13 | 2.2 | 4.1 |
| Comp. Ex. 14 | 1.9 | 4.8 |
| Comp. Ex. 15 | 74.9 | 574.9 |

COMPARATIVE EXAMPLES 14 AND 15

The Renault R14 Engine test was repeated using a fully formulated motor oil containing 1.4 wt % ZDDP (Comp. 14) and one containing 0.59 wt % ZDDP (Comp. 15). The results are shown in Table III.

EXAMPLE 16

In this example, a valve train wear test was conducted using a motored 2.3 liter Ford engine.

This motored test was carried out for 60 hours with camshaft speeds ranging from 200 to 1000 RPM. Continuous cam shaft torque measurements were made while running the wear tests. These torque measurements provide a measure of friction reducing capability of the lubricating oil and therefore of the potential of the additives in the oil to provide fuel economy.

The SAE 10W30 oil tested contained 36% of the normal concentration of ZDDP used in passenger car engine oils and 0.5 wt. % of the additive of Example 3. Sufficient t-butyl hydroperoxide was added to the oil when tested to provide an initial hydroperoxide number (HPN) of 90, HPN defined as millequivalents of oxygen per kilogram of sample.

After 60 hours, the average cam lobe wear was only 10 microns.

Also, the oil containing the additive of this invention shows significant reduction in torque relative to oils which do not contain it demonstrating significant reduction in friction.

COMPARATIVE EXAMPLE 17

The test of Example 16 was repeated, except that the oil did not contain the additive of this invention. The cam lobe wear in this run was 21 microns.

EXAMPLE 18

This example shows that the friction reducing properties of $Mo_4S_4(S_2COR)_6$ are markedly superior to conventional function modifying additives.

Friction measurements performed in a ball on cylinder friction tester showed that $Mo_4S_4(S_2COR)_6$ where R in this case is the octyl radical is markedly superior in reducing friction than conventional friction reducing agents such as stearic acid. This test employs a 12.5 mm diameter stationary ball and a rotating cylinder 43.9 mm in diameter. Both components were made from AISI 52100 steel. The steel balls were used in the heat treated condition with a Vickers hardness of 840, the cylinders used in the normalized condition with a Vickers hardness of 215.

The cylinder rotates inside a cup containing sufficient quantity of lubricant such that 2 mm of the cylinder bottom is submerged. The lubricant is carried to the ball contact by the rotation of the cylinder.

A normal force of 9.8N was applied to the ball through dead weights, the cylinder rotated at 0.25 RPM to ensure boundary lubrication conditions prevailed.

The friction force was continuously monitored through a load transducer by measuring the tangential force on the ball. Friction coefficients attain steady state values after 7 to 10 turns of the cylinder.

It is well known that stearic acid is an excellent friction modifier. Under the conditions stated above, the minimum friction coefficient obtained with stearic acid in hexadecane is 0.077. With 0.5 wt. % $Mo_4S_4(S_2CO\text{-octyl})_6$, the friction coefficient is 0.022, exceptionally low friction under boundary lubrication conditions. Commercial friction modifiers in these ball on cylinder tests exhibit friction coefficients ranging from 0.12 to 0.14.

EXAMPLES 19 AND 20

In these examples, several different tests were conducted to evaluate the oxidation protection activity of the additives of the present invention. These tests were conducted on oil formulations similar to the formulations described in Example 2.

One test, termed the lube stability test, was carried on as follows: a sample of the oil was oxidized by sparging air through it at 172° C. in the presence of Cu-Pb and Ag bearing specimens. The air flow rate was one liter per minute. The test results are reported as a percent viscosity increase (kinematic viscosity at 40° C., and at −20° C. cold cranking simulator, (CCS). Cumulative weight losses of the Cu-Pb and Ag bearings were determined over varying time intervals. The test was conducted for a total of 46 hours and the results at that time interval are shown in Table IV.

In another test, a differential scanning (DSC) calorimetry test, a sample of the oil is heated in air at a programmed rate, e.g., 5° C./minute, and the sample temperature rises relative to an inert reference was measured. The temperature at which an exothermic reaction (the oxidation onset temperature) is a measure of oxidative stability of the sample. The results of these tests are also shown in Table IV.

COMPARATIVE EXAMPLES 21 AND 22

Following the test procedures of Examples 19 and 20, a Solvent 150 Neutral oil (Comp. Ex. 21) and a commercially formulated oil (Comp. Ex. 22) were tested for comparative purposes with the results shown in Table IV.

TABLE IV

| Test Run | Oil | 46 Hr Lube Stability Test | | | | DSC Oxidation onset Temp., °C. |
|---|---|---|---|---|---|---|
| | | Viscosity Increase % KVIC | CCS | Cumulative Wt Loss (mg) | | |
| | | 40° C. | −20° C. | Cu—Pb | Ag | |
| (1) Ex. 19 | S150N + 10% Ex. 1 additive | 9 | N/M[2] | −5[3] | 0.3 | 266 |
| (2) Ex. 20 | Commercially available oil without ZDDP and oxidants but with 1% Ex. 1 additive | 11 | 2 | −26[3] | 11.5 | 276 |
| (3) Comp. Ex. 21 | S150N | Solid | Solid | N/T[1] | N/T[1] | 210 |
| (4) Comp. Ex. 22 | Commercially available oil containing ZDDP and oxidants | 19 | 74 | 112 | 77.3 | 266 |

[1]N/T = not tested
[2]N/M = not measured
[3]— Minus sign signifies weight gain

What is claimed is:

1. A lubricating oil composition comprising: an oil of lubricating viscosity and an additive formed by contacting molybdenum hexacarbonyl with a dixanthogen of the formula $(ROCS_2)_2$ for a time sufficient to form the additive, wherein R is an organo group having a sufficient number of carbon atoms to render the additive soluble in the oil.

2. The composition of claim 1 wherein R is selected from alkyl, aralkyl and alkoxylalkyl groups having from about 2 to about 20 carbon atoms.

3. The composition of claim 2 wherein R is an alkyl group of from about 4 to 12 carbon atoms.

4. The composition of claim 1 wherein the contacting is conducted at temperatures of from ambient temperatures to about 140° C.

5. The composition of claim 4 wherein the contacting is conducted at temperatures of about 80° C. to about 120° for about 2 hours to about 10 hours.

6. The composition of claim 5 wherein the mole ratio of dixanthogen to molybdenum hexacarbonyl is in the range of from about 1.5:1 to about 2:1.

7. The composition of claim 6 wherein the additive is present in an amount ranging from about 0.01 to about 2.0 weight percent based on the weight of the oil.

8. The composition of claim 7 wherein the amount is in the range of from 0.1 to 1.0 weight percent.

9. A lubricating composition comprising: an oil of lubricating viscosity; and an additive having the formula $Mo_4S_4(S_2C-OR)_6$ wherein R is selected from organo groups having sufficient number of carbon atoms to render the additive soluble in oil.

10. The lubricating composition of claim 9 wherein R is selected from alkyl, aralkyl and alkoxylalkyl groups having from about 2 to about 20 carbon atoms.

11. The lubricating composition of claim 10 wherein the amount of the additive is in the range of from about 0.01 to about 2.0 weight percent based on the weight of oil.

12. A lubricating oil composition comprising: a major amount of an oil selected from natural and synthetic oils having lubricating viscosities; and, from about 0.01 to about 2.0 weight percent of an additive formed by reacting a dixanthogen and $Mo(CO)_6$ in the mole ratio of from about 1.5:1 to about 2:1 at temperatures of from about 80° C. to about 120° C. for from about 2 hours to about 10 hours, the dixanthogen having the formula $(ROCS_2)_2$ wherein R is selected from alkyl, aralkyl and alkoxylalkyl groups having from about 2 to about 20 carbon atoms.

13. The composition of claim 12 wherein R is an alkyl group of from about 4 to 12 carbon atoms.

14. An additive concentrate for blending with lubricating oils to provide lubricating composition having improved wear, friction, and oxidation properties comprising: a hydrocarbon diluent and from about 1 to about 90 weight percent of a compound formed by reacting a dixanthogen and $Mo(CO)_6$ in the mole ratio of from about 1.5:1 to about 2:1 at temperatures of from about ambient temperature to about 140° C. for from about 2 hours to about 10 hours, the dixanthogen having the formula $(ROCS_2)_2$ wherein R is selected from alkyl, aralkyl and alkoxylalkyl groups having from about 2 to about 20 carbon atoms.

15. The concentrate of claim 14 wherein the hydrocarbon diluent is selected from hydrocarbons in which the additive is soluble.

16. The concentrate of claim 15 wherein the compound formed by reacting a dixanthogen and $Mo(CO)_6$ is present in from about 30 to about 60 weight percent.

17. A method of preparing a lubricating oil additive comprising: contacting a dixanthogen and $Mo(CO)_6$ in the mole ratio of from about 1.5:1 to about 2:1 at temperatures of from about ambient temperature to about 140° C. for from about 2 hours to about 10 hours, the dixanthogen having the formula $(ROCS_2)_2$ wherein R is selected from alkyl, aralkyl and alkoxylalkyl groups having from about 2 to about 20 carbon atoms.

18. The method of claim 17 wherein the temperature ranges from about 80° C. to about 120° C.

19. The method of claim 18 wherein the contacting is conducted in the presence of an aromatic hydrocarbon.

20. The method of claim 19 wherein the hydrocarbon is toluene.

* * * * *